United States Patent [19]
DiNovi et al.

[11] Patent Number: 4,871,776
[45] Date of Patent: * Oct. 3, 1989

[54] 2,5-ANHYDRO-1,6-DIHALO-1,6-DIDEOXY-D-MANNITOL

[75] Inventors: Michael J. DiNovi, Philadelphia, Pa.; Robert J. Rafka, Groton Long Point, Conn.; Mark I. Friedman, Merion; Michael G. Tordoff, Philadelphia, both of Pa.

[73] Assignee: Monell Chemical Senses Center, Philadelphia, Pa.

[*] Notice: The portion of the term of this patent subsequent to Feb. 28, 2006 has been disclaimed.

[21] Appl. No.: 112,260

[22] Filed: Oct. 22, 1987

Related U.S. Application Data

[63] Continuation-in-part of Ser. No. 910,698, Sep. 23, 1986, Pat. No. 4,808,626.

[51] Int. Cl.$^4$ ............................................. A61K 31/045
[52] U.S. Cl. .................................... 514/738; 514/910; 536/1.1; 536/122
[58] Field of Search ....................... 514/738, 910, 473; 536/1.1, 122

[56] References Cited

U.S. PATENT DOCUMENTS 4,808,626  2/1989  Friedman ............................ 514/738

OTHER PUBLICATIONS

Kissileff, H. R. et al., "Physiology of the Control of Food Intake", *Ann. Rev. Nutri.*, 2:371–418 (1982).
Russek, M., "Current Status of the Hepatostatic Theory of Food Intake Control", *Appetite*, 2:137–143 (1981).
Friedman, M. I. et al., "The Physiological Psychology of Hunger: A Physiological Perspective", *Physiological Review*, 83(6): 409–431 (1976).
Riquelme, P. T. et al., "Mechanism of Action of 2,5-Anhydro-D-Mannitol in Hepatocytes", *Journal of Biological Chemistry*, 259(8): 5115–5123 (Apr. 25, 1984).
Stevens, H. C. et al., "2,5-Anhydro Mannitol Inhibits Gluconeogenesis from Dihydroxyacetone in Rat Hepatocytes", *Fed. Proc.*, 42, Part 2, Abstract No. 2384 (1983).
Stevens, H. C. et al., "2,5-Anhydro-D-Mannitol Inhibits Glycogenolysis in Isolated Rat Hepatocytes", *Fed. Proc.*, 40, Part 1, Abstract 3479 (1981).
Hanson, R. L. et al., "Hypoglycemic Effect on 2,5-Anhydro-D-Mannitol", *Fed. Proc.*, 42 (Part 1), Abstract No. 1453 (1983).
Raushel, F. M. et al., "The Substrate and Anomeric Specificity of the Fructokinase", *Journal of Biological Chemistry*, 248(23):8174–8177 (Dec. 10, 1973).
Riquelme, P. T. et al., "Inhibition by 2,5-Anhydromannitol of Glycolysis in Isolated Rat Hepatocytes and in Ehrlich Ascites Cells", *Proc. Natl. Acad. Sci. U.S.A.*, 82:78–82 (Jan. 1985).
Riquelme, P. T. et al., "Regulation of Carbohydrate Metabolism by 2,5-Anhydro-D-Mannitol", *Proc. Natl. Acad. Sci. U.S.A.*, 80:4301–4305 (Jul. 1983).
Hanson, R. L. et al., "Inhibition of Gluconeogenesis and Glycogenolysis by 2,5Anhdro-D-Mannitol", *Journal of Biological Chemistry*, 259(1):218–223 (Jan. 10, 1984).

*Primary Examiner*—William R. Dixon, Jr.
*Assistant Examiner*—Anthony J. Green
*Attorney, Agent, or Firm*—Woodcock Washburn Kurtz Mackiewicz & Norris

[57] ABSTRACT

A novel fructose analog is disclosed which has been found to modify the food intake of mammals. If administered during the diurnal fasting period, the mammals increase their food intakes. If administered during the diurnal feeding period, food intake is decreased. The compound is 2,5-anhydro-1,6-dihalo-1,6-dideoxy-D-mannitol, preferably 2,5-anhydro-1,6-dichloro-dideoxy-D-mannitol ("Charmitol").

12 Claims, 1 Drawing Sheet

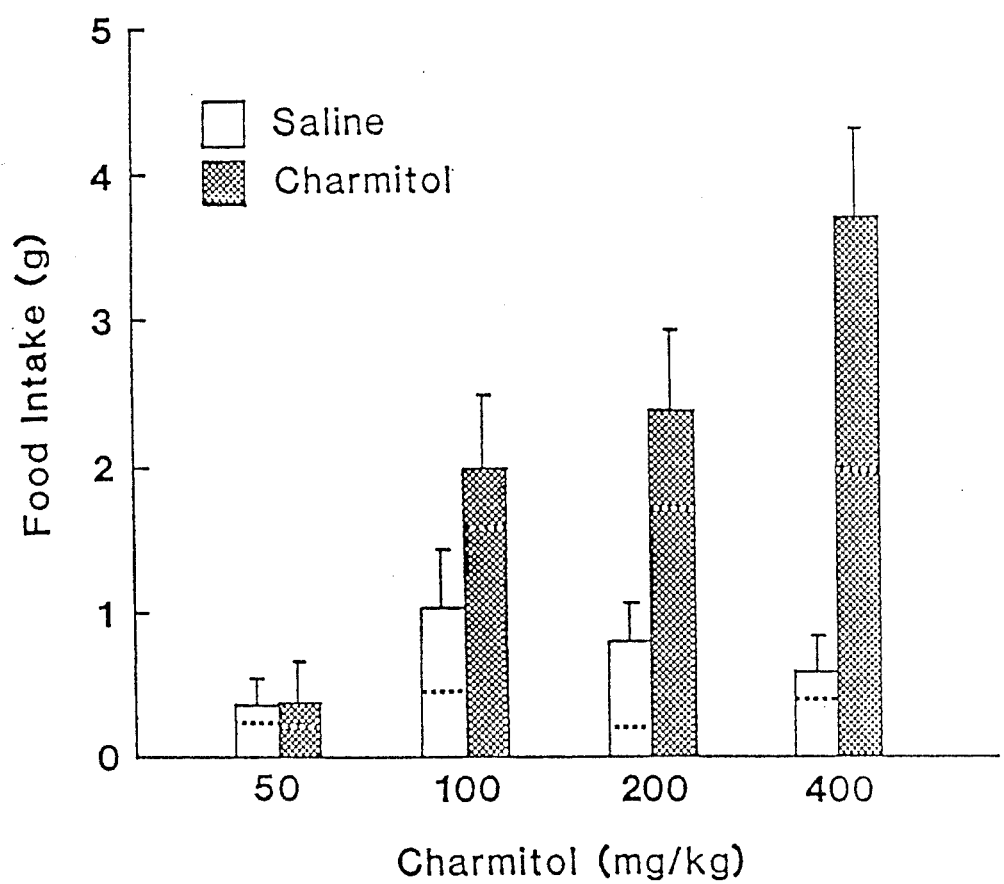

2,5-ANHYDRO-1,6-DIHALO-1,6-DIDEOXY-D-MANNITOL

CROSS REFERENCE TO RELATED APPLICATIONS

This application is a continuation-in-part of our prior, co-pending related U.S. application, Ser. No. 910,698, filed Sep. 23, 1986, now U.S. Pat. No. 4,808,626, entitled "Use of 2,5-anhydro-D-mannitol as a Food Intake Modifier" which is incorporated herein by reference as if fully set forth.

BACKGROUND OF THE INVENTION

The present invention relates to the field of food intake modifiers, and more particularly to the field of modifiers that can be administered to increase or decrease mammalian food intake.

The physiology of the control of food intake is not well understood. Many cogent theories have been advanced based on data and observation. Several of these theories are discussed in "Physiology of the Control of Food Intake", Kissileff et al, *Ann. Rev. Nutr.*, 2:371-418 (1982); Russek "Current Status of the Hepatostatic Theory of Food Intake Control", *Appetite*, 2:137-143 (1981); and Friedman et al, "The Physiological Psychology of Hunger: A Physiological Perspective", *Physiological Review*, 83(6):409-431 (1976). Notwithstanding the current knowledge in this area, the effect that the administration of any given substance will have upon a mammal's food intake is normally difficult if not impossible to predict in the absence of significant food intake data stemming from prior experience with that compound or substance.

The present invention relates in particular to the effects of a dichloro derivative of 2,5-anhydro-D-mannitol and its effect on the food intake behavior of mammals. 2,5-anhydro-D-mannitol is a known fructose analog. The literature contains several reports concerning the possible biochemical and/or metabolic effects of 2,5-anhydro-D-mannitol (hereinafter referred to as 2,5-AM). See Riquelme et al, "Mechanism of Action of 2,5-anhydro-D-mannitol in Hepatocytes", *Journal of Biological Chemistry*, 259(8):5115-5123 (Apr. 25, 1984); Stevens et al, "2,5-anhydro-mannitol Inhibits Gluconeogenesis from Dihydroxyacetone in Rat Hepatocytes", *Fed. Proc.* 42 (Part II) Abstract No. 2384 (1983); Stevens et al, "2,5-anhydro-D-mannitol Inhibits Glycogenolysis in Isolated Rat Hepatocytes", *Fed. Proc.* 40 (Part I) Abstract No. 3479 (1981); Hanson et al, "Hypoglycemic Effect of 2,5-anhydro-D-mannitol", *Fed. Proc.* 42 (Part II), Abstract No. 1453 (1983); Raushel et al, "The Substrate in Anomeric Specificity of Fructokinase", *Journal of Biological Chemistry*, 248(23):8174-8177 (Dec. 10, 1973); Riquelme et al, "Inhibition by 2,5-anhydro-mannitol of Glycolysis in Isolated Rat Hepatocytes and in Ehrlich Ascites Cells", *Proc. Natl. Acad. Sci. U.S.A.*, 82:78-82 (January, 1985) Riquelme, "Regulation of Carbohydrate Metabolism by 2,5-anhydro-D-mannitol", *Proc. Natl. Acad. Sci. U.S.A.*, 80:4301-4305 (July, 1983); and Hanson et al, "Inhibition of Gluconeogenesis and Glycogenolysis by 2,5-anhydro-D-mannitol", *Journal of Biological Chemistry*, 259(1):218-223 Jan. 10, 1984). While most of these papers address the effect of 2,5-AM at cellular and intracellular levels, please note that Hanson et al (1984) discloses the administration of 2,5-AM to fasting mice and rats. Hanson et al fails to report any food intake data, nor does Hanson suggest what effect, if any, 2,5-AM might have in altering food intake.

Since 2,5-AM can be phosphorylated, one possible side effect of its use is ATP depletion. A need thus exists for substances to treat overeating or obesity, and/or anorexia or other conditions exhibiting a reduced appetite, which are less likely to exhibit undesirable side effects, such as ATP depletion.

SUMMARY OF THE INVENTION

The present invention provides a novel method for altering the food intake of a mammal comprising administering 2,5-anhydro-1,6-dihalo-1,6-dideoxy-D-mannitol, preferably 2,5-anhydro-1,6-dichloro-1,6-dideoxy-D-mannitol ("Charmitol") to said mammal in an amount sufficient to alter the food intake of said mammal. Charmitol cannot be phosphorylated, and thus does not present a risk of producing serious ATP depletion.

A preferred embodiment of the present method comprises dentifying the diurnal feeding and fasting periods of the animal to be treated. (Fasting is defined as a period of 2 or more hours without food or with food restricted). If an increase in food intake is desired, Charmitol is administered from up to two hours in advance of that fasting period to up to two hours from the expected conclusion of that fasting period to increase food intake during that fasting. If it is desired to reduce food intake, said Charmitol is administered within two hours in advance of the onset of the identified diurnal feeding period to decrease the food intake during that period. The subject method also applies to mammals having irregular feeding habits, such as anotoxic mammals. Preferably, at least 50 mg/kg of said mannitol is administered to said mammal, more preferably 200-400 mg/kg, although the lower and upper limits of administration have not yet been determined. The dosages were determined with rat tests. Those skilled in the art will recognize that the exact dosages for other mammals may differ.

Quite surprisingly, applicants have found that, depending upon the time of administration with respect to the mammal's feeding schedule, be it diurnal or irregular, the subject mannitol may either increase or decrease food intake. Such administrations have been found to be effective when administered by the intragastric route.

It is not presently understood why the subject Charmitol exhibits the observed effect on food intake. It is currently theorized that the increase in hunger during fasting periods, when the mammal relies on its stored sources of fuels, probably reflects inhibition of gluconeogenesis and glycogenolysis. The decrease in hunger during feeding periods, when the mammal utilizes exogenous fuels, probably reflects Charmitol induced enhancement of glycolysis. The administration of Charmitol thus holds promise as an orally-effective, peripherally-acting fructose analogue that may have therapeutic and other applications as a modulator of food intake when prescribed for a variety of different conditions.

Accordingly, a primary object of the present invention is the provision of a method of food intake modification to selectively increase or decrease mammalian food intake.

This and other objects of the present invention will become apparent from the following, more detailed description.

BRIEF DESCRIPTION OF THE DRAWINGS

FIG. 1 is a bar chart showing food intake of rats given Charmitol during the diurnal fast; P being less than 0.05 relative to the saline control; the dotted lines separating intake from the first two hours of the test from intake during the following three hours.

DESCRIPTION OF THE PREFERRED EMBODIMENTS

The present invention provides a novel method of modifying the appetite of mammals by feeding Charmitol to treat overeating, obesity or anorexia. In treating overeating or obesity, a dihalogenated fructose analog such as Charmitol is administered at or within two hours of an identified feeding period (mealtime) to depress the appetite. In treating anorexia or other conditions exhibiting a reduced appetite, the subject material is administered within up to two hours from the beginning of through two hours from the end of an identified fasting (between meals). Accordingly, depending upon the time of administration, the subject material accelerates growth or fosters a loss or gain of body weight and/or fat content. Although the normal feeding or fasting periods are preferably determined by identifying the diurnal feeding schedule of a mammal on a regular feeding schedule, the present method has applicability to determined feeding or fasting periods of irregular schedules as well, such as those of anorexic mammals.

In order to achieve the intended effect, it is first necessary to determine the feeding patterns, and more particularly, the next feeding or fasting period, of the mammal whose food intake is to be altered. Preferably, the diurnal feeding pattern of a mammal on a regular feeding schedule is determined. For most humans, the identification of diurnal feeding and fasting periods is fairly simple. This will normally consist of 2-4 mealtimes per day between which are fasting periods or various durations. Other mammals also have identifiable feeding and fasting periods. Rats are nocturnal, normally fasting during the day, and depending upon the availability of a food source, feeding relatively continuously throughout the night. Dogs and cats similarly have identifiable feeding and fasting periods, which may vary somewhat from animal to animal, as have other mammals, such as cows, horses, sheep and other livestock. To demonstrate the effectiveness of the present invention, the following exemplary tests were performed:

We have shown previously that an analogue of B-D-fructofuranose, 2,5-anhydro-D-mannitol (2,5-AM), increased food intake of rats when administered during the diurnal fast, but decreased intake when administered during the nocturnal feeding period. Although, evidence from in vitro experiments suggests that 2,5-AM can influence carbohydrate metabolism in the liver, it is unclear how these changes can account for its dichotomous effect on food intake. It is known that 2,5-AM is phosphorylated to 2,5-AM-1-phosphate and 2,5-AM-1,6-bisphosphate, which are apparently not metabolized further. Consequently, it is likely that these phosphorylated intermediates accumulate in the liver and they could possibly act as a "phosphate trap", by sequestering phosphate necessary for other metabolic processes. This has been demonstrated to occur after supraphysiological infusions of the parent compound, fructose (e.g. Niewoehner, C. B., *J. Amer. Colleqe. Nutr.*, 5:443-450 1986).

To examine whether phosphorylation is required for 2,5-AM to affect food intake we have synthesized and tested the 2,5-AM analogue, 2,5-anhydro-1,6-dichloro-1,6-dideoxy-D-mannitol (referred to as Charmitol, for brevity). The molecular structure of this compound strongly suggests it cannot be phosphorylated. We have examined the effects of Charmitol on food intake in rats tested during both diurnal fasting and nocturnal feeding.

Methods

Synthesis

Charmitol was prepared in one step from 2,5-AM using the selective chlorination method of Whistler et al, *Carbohydrate Research*. 61:511-518, 1978), which publication is hereby incorporated herein by reference. A solution of 125 mg 2,5-AM in 5.0 ml pyridine was cooled to 0° C. Four equivalents of triphenylphosphine were added followed by two equivalents of carbon tetrachloride. After stirring overnight at room temperature the reaction was quenched with methanol, concentrated to dryness several times with toluene, and purified by chromatography on silica gel. The yield was 96 mg (62%). Further purification was achieved by recrystallization from a minimum volume of dichloromethane at reflux temperature.

Procedure

Male Sprague Dawley CD rats (Charles River, Wilmington, Mass.) were individually housed in stainless steel cages with ad libitum access to Purina Laboratory Chow (#5001) and tap water. Temperature was maintained at approximately 21° C. and a 12:12 h light/dark cycle was imposed. Rats were adapted to vivarium conditions for at least a week before tests began.

At the start of the experiments, the 12 rats in the diurnal test weighted 289-322 g and the nine rats in the nocturnal test weighted 274-324 g. In both studies, rats received ascending doses of Charmitol (50, 100, 200 and 400 mg/kg) by intragastric intubation (2 ml/kg). Each of the four doses had its own isotonic saline control intubation, given in counterbalanced order, so that on any test half the rats received saline and the other half received Charmitol. Tests were conducted every 3-4 days. Intubations were given 5 h after lights on for rats tested during the day, and as the lights went off for rats tested at night. Food intake (±0.1 g) was recorded hourly (under dim red illumination at night) for the 5 h after intubation and after 24 h.

Results were analyzed by analysis of variance for each cumulative time period, with Charmitol (saline v. Charmitol) and Dose (100, 200, and 400 mg/kg) as factors. Significant effects were analyzed further using post hoc t-tests. Probability cut-offs were set at $p<0.05$.

Results

Diurnal Tests

Rats ate significantly more when given Charmitol than when given saline during the entire 5-h test period, $F(1,11)=17.5$, $p<0.005$, and during each cumulative hour of the test (all p's $<0.005$). During the first hour, the overall effect of Charmitol was to increase food intake, $F(1,11)=17.5$, $p<0.001$, but there were no significant differences between food intakes after the four doses of Charmitol. At later times, however, there were dose-related effects. For example, during the first 2 h of the test, the 50 mg/kg dose of Charmitol did not significantly increase food intake relative to intake after saline intubation but the other three doses did, leading to a significant Charmitol × Dose interaction, $F(3,33)=3.19$, $p<0.05$. After 5 h, the 100, 200, and 400 mg/kg doses increased food intake significantly more than did saline or the 50 mg/kg intubation. In addition, the 400 mg/kg dose increased food intake significantly more than did the 100 mg/kg dose.

After 24 h, food intake was not significantly affected by the various treatments, although there was a marked tendency for 24-h intakes after the 400 mg/kg dose of Charmitol to be lower than those after saline (means± SEMS (g) for saline=21.4±0.99, 400 mg/kg Charmitol=18.0±1.19).

Nocturnal Tests

There were no significant effects of Charmitol on food intake during the first 2 h of the nighttime test, and if anything Charmitol tended to increase food intake (see Table 1). However, Charmitol significantly decreased food intake in the 3rd-5th hours, (intake during this 2 h period, $F(1,8)=11.7$, $p<0.01$; cumulative intake for the 3rd h, $F(1,8)=9.18$, $p<0.05$; 4th h, $F(1,8)=16.0$, $p<0.005$; 5th h $F(1,8)=17.8$, $p<0.005$). There was a tendency for this decrease to be greater after higher doses of Charmitol, although this was not a significant effect. The results are set forth in Table 1:

TABLE 1

Cumulative Food Intake After Nighttime Administration of Charmitol

| Dose mg/kg | 2 h | | 5 h | |
|---|---|---|---|---|
| | Saline | Charmitol | Saline | Charmitol |
| 50 | 2.5 ± 0.38 | 1.9 ± 0.56 | 6.2 ± 0.96 | 4.3 ± 0.98* |
| 100 | 3.4 ± 0.56 | 2.9 ± 0.48 | 8.5 ± 0.77 | 5.7 ± 0.78* |
| 200 | 2.6 ± 0.55 | 3.2 ± 0.41 | 6.9 ± 0.88 | 6.0 ± 0.62 |
| 400 | 3.1 ± 0.35 | 3.7 ± 0.68 | 8.7 ± 0.85 | 6.0 ± 0.58* |

*Note $p < 0.05$ relative to intake after saline intubation. Saline or Charmitol was intubated at the beginning of the dark period and food intake (g) was measured at various times. n = 9

After 24 h, the overall effect of Charmitol was to decrease food intake, $F(1,8)=13.4$, $p<0.01$, (average 24-h intake after saline=22.6±0.54 g, after Charmitol=17.7±1.24 g). The difference between intake after saline and after Charmitol was progressively larger as the dose of Charmitol increased, but this trend for a dose-related decrease was not statistically significant.

Discussion

Charmitol produced a dose-related increase in feeding when administered during the diurnal fast but decreased feeding when administered at the start of the nocturnal feeding period. The direction and magnitude of its effects were similar to those of 2,5-AM, suggesting that phosphorylation or "phosphate trapping" is not required for 2,5-AM and its analogues to influence food intake.

Given the similar effects on food intake of Charmitol and 2,5-AM it is likely they will have similar possible uses (i.e., increase food intake of anorexic patients, livestock, etc. and decrease the food intake of the obese, etc.).

A possible practical application unique to Charmitol is that it may provide a useful method of enhancing the appetite of patients with various ailments (e.g. anorexia nervosa, gastrointestinal disease, liver disease) that require intravenous nutrition (e.g. total parenteral nutrition). Fructose is more rapidly metabolized than is glucose, and its uptake into cells is relatively independent of insulin. This suggests that fructose would be a better agent for intravenous feeding than glucose, although as fructose can sequester phosphate, it has limited application as a nutrient for intravenous nutrition. As Charmitol is an analogue of fructose, it is probably metabolized rapidly. As it cannot be phosphorylated, it may well modify food intake without the possibly deleterious effects of phosphate sequestration produced by intravenous fructose and perhaps by 2,5-AM Conclusion Accordingly, it will be seen that a novel method of altering the food intake of a mammal is provided which is effective to selectively increase or decrease the amount of food consumed by that mammal, depending upon the time of administration of Charmitol relative to the determined feeding or fasting schedule of the mammal.

What is claimed is:

1. A novel composition useful for modifying the food intake of mammals, comprising:
2,5-anhydro-1,6-dihalo-1,6-dideoxy-D-mannitol.

2. The composition of claim 1 wherein said halo groups are chloro groups.

3. A method of modifying the food intake in mammals consisting essentially of the step of administering to said mammals an amount of 2,5-anhydro-1,6-dihalo-1,6-dideoxy-D-manniol effective to modify said food intake.

4. The method of claim 3 wherein said method consists essentially of administering 2,5-anhydro-1,6-dichloro-1,6-dideoxy-D-mannitol.

5. The method of claim 3 wherein said amount is at least 50 mg/kg per administration.

6. The method of claim 5 wherein said amount is administered intragastrically.

7. The method of claim 6 wherein said amount is about 50-400 mg/kg per administration.

8. The method of claim 4 wherein said method of modifying is a method of increasing the food intake, and wherein said step of administering comprises administering during a diurnal fasting period.

9. The method of claim 8 wherein said method comprises administering said mannitol within two hours in advance of the onset of said diurnal fasting period.

10. The method of claim 4 wherein said method of modifying is a method of decreasing the food intake, and wherein said step of administering comprises administering during a diurnal feeding period.

11. The method of claim 10 wherein said method comprises administering said mannitol within two hours in advance of the onset of said diurnal feeding period.

12. A method of making 2,5-anhydro-1,6-dichloro-1,6-dideoxy-D-mannitol consisting essentially of the steps of:
(a) providing 2,5-anhydro-D-mannitol;
(b) halogenating the compound of step (a) by contacting it under reaction conditions with triphenylphosphine and carbon tetrachloride to produce 2,5-anhydro-1,6-dichloro-1,6-dideoxy-D-mannitol.

* * * * *